(12) United States Patent
Kovesdi et al.

(10) Patent No.: US 6,821,775 B1
(45) Date of Patent: Nov. 23, 2004

(54) VIRAL VECTOR ENCODING PIGMENT EPITHELIUM-DERIVED FACTOR

(75) Inventors: Imre Kovesdi, Rockville, MD (US); Douglas E. Brough, Olney, MD (US); Duncan L. McVey, Derwood, MD (US); Lisa Wei, Gaithersburg, MD (US)

(73) Assignee: GenVec, Inc., Gaithersburg, MD (US)

( * ) Notice: Subject to any disclaimer, the term of this patent is extended or adjusted under 35 U.S.C. 154(b) by 0 days.

(21) Appl. No.: 09/599,997

(22) Filed: Jun. 23, 2000

Related U.S. Application Data

(60) Provisional application No. 60/181,743, filed on Feb. 11, 2000.

(51) Int. Cl.⁷ ............................................. C12N 15/861
(52) U.S. Cl. .................................................. 435/320.1
(58) Field of Search ......................... 435/320.1; 514/44

(56) References Cited

U.S. PATENT DOCUMENTS

| | | | | |
|---|---|---|---|---|
| 5,583,009 A | * | 12/1996 | Palmiter et al. | 435/69.1 |
| 5,641,749 A | | 6/1997 | Yan et al. | |
| 5,710,136 A | | 1/1998 | Robinson et al. | |
| 5,770,580 A | | 6/1998 | Ledley et al. | |
| 5,792,751 A | | 8/1998 | Ledley et al. | |
| 5,801,156 A | | 9/1998 | Robinson et al. | |
| 5,827,702 A | | 10/1998 | Cuthbertson | |
| 5,840,686 A | | 11/1998 | Chader et al. | |
| 5,962,311 A | * | 10/1999 | Wickham et al. | 435/320.1 |
| 6,113,913 A | * | 9/2000 | Brough et al. | 424/233.1 |
| 6,204,251 B1 | | 3/2001 | Cuthbertson | |
| 6,225,113 B1 | * | 5/2001 | Brough et al. | 435/320.1 |
| 6,228,646 B1 | * | 5/2001 | Hardy | 435/455 |
| 6,288,024 B1 | * | 9/2001 | Bouck et al. | 514/2 |

FOREIGN PATENT DOCUMENTS

| | | |
|---|---|---|
| WO | WO93/24529 A | 12/1993 |
| WO | WO94/01139 A | 1/1994 |
| WO | WO94/20146 A | 9/1994 |
| WO | WO95/33480 A | 12/1995 |
| WO | WO97/37542 A | 10/1997 |
| WO | WO98/49321 A | 11/1998 |
| WO | WO99/04806 A | 2/1999 |
| WO | WO99/26480 A | 6/1999 |
| WO | WO99/29345 A | 6/1999 |
| WO | WO00/15822 A | 3/2000 |
| WO | WO00/54813 A | 9/2000 |

OTHER PUBLICATIONS

Wang et al., Nature Medicine, Jun., 1996, vol. 2, No. 6, pp. 714–716.*
Aiello, *PNAS USA,* 92 (23), 10457–10461 (Nov. 1995).
Kendall et al., *PNAS USA,* 90 (22), 10705–10709 (Nov. 1993).
Pignolo et al.,*J. Biol. Chem.,* 268 (12), 8949–8957 (Apr. 25, 1998).
Dawson et al., *Science,* 285, 245–248 (Jul. 9, 1999).
Steele et al., *PNAS USA, 90,* 1526–1530 (Feb. 1993).

* cited by examiner

*Primary Examiner*—Terry McKelvey
(74) *Attorney, Agent, or Firm*—Leydig, Voit & Mayer, Ltd.

(57) ABSTRACT

The present invention provides a viral vector comprising a nucleic acid sequence encoding pigment epithelium-derived factor (PEDF) or a therapeutic fragment thereof. The nucleic acid sequence is operably linked to regulatory sequences necessary for expression of PEDF or a therapeutic fragment thereof. Preferably, the viral vector is an adenoviral vector or an adeno-associated viral vector. Also preferably, the viral vector further comprises one or more additional nucleic acid sequences encoding therapeutic substances other than PEDF.

15 Claims, No Drawings

US 6,821,775 B1

VIRAL VECTOR ENCODING PIGMENT EPITHELIUM-DERIVED FACTOR

CROSS-REFERENCE TO RELATED PATENT APPLICATIONS

This patent application claims the benefit of U.S. provisional patent application 60/181,743, filed Feb. 11, 2000.

TECHNICAL FIELD OF THE INVENTION

The present invention relates to a viral vector comprising a nucleic acid encoding pigment epithelium derived factor.

BACKGROUND OF THE INVENTION

Gene therapy is the next best hope for the treatment and prevention of a broad array of human diseases. Since the first gene therapy clinical trials started in 1990, more than 300 clinical protocols have been approved and an estimated $200 million is spent by the National Institutes of Health (NIH) to develop the tools and techniques necessary to practice gene therapy (Marshall, *Science*, 269, 1050–1055 (1995); and Anderson, *Nature*, 392, 25–30 (1998)). The potential of treating disease at its most basic level is staggering. Yet, many hurdles exist in genetic research before the unlimited potential of gene therapy can be realized in the clinic. Obstacles associated with the wide-spread acceptance of gene therapy include obtainment of long term gene expression, efficient nucleic acid delivery, transduction of both dividing and non-dividing cells, target cell specificity, safety, and construction of inexpensive expression vectors for use in gene therapy protocols. Gene therapy research can be divided into two major areas: techniques and tools. Gene therapy techniques that are currently under study include methods of gene transfer in vivo and ex vivo, cell culture methods, methods of identifying appropriate target cells, methods of quantifying and qualifying gene expression in vivo, and the like.

In addition to perfecting techniques employed in gene therapy, much research has been focused on the tools of gene transfer for the purpose of treating or preventing disease. Many in the art have called for additional research into the improvement of gene transfer vectors, regulatory sequences, and producer cell lines. A great deal of enthusiasm surrounds the use of synthetic gene delivery vehicles and naked DNA. In fact, the first expression vector used for gene transfer was naked DNA. Naked DNA, e.g., plasmids, have virtually unlimited capacity and are relatively simple to construct. Plasmids are genetically engineered circular double-stranded DNA molecules that are inexpensive and easy to produce, and can transduce any type of gene or functional nucleic acid into cells. Yet, the level of expression efficiency of plasmids is poor, plasmids are not easily taken up by host cells, and plasmids are easily degraded when exposed to high temperatures, enzymes, chemicals, mechanical stress, and the like. Thus, to increase the efficiency of gene transfer and vector stability, naked DNA is often complexed with liposomes or other molecules. Liposomes are vesicle-type structures wherein fluid is encapsulated by a lipid bilayer. While the liposomes used for plasmid-mediated gene transfer strategies have various compositions, they are typically synthetic cationic lipids. Due to the negative charge of DNA, naked DNA is attracted to the positively-charged surface of liposomes. Naked DNA also can be conjugated to other molecules, such as proteins, in order to facilitate DNA uptake. The proteins associated with DNA allow targeting of the nucleic acid molecule to a particular cell type, as well as increase plasmid uptake. Liposome- and molecular conjugate-mediated gene transfer is a great deal more efficient than transfection of non-complexed, naked DNA.

Clearly, several advantages exist in using naked DNA in gene therapy protocols. Plasmids are largely undetected by the body's innate immune system and, therefore, are not readily cleared by the body. In addition, plasmids are non-infectious and are rarely mutagenic. As such, naked DNA is believed by some to be the ideal mode of gene transfer for purposes of gene therapy. Yet, even when complexed with facilitators, efficiency of host cell transfection and subsequent expression of transgenes is relatively low. For instance, although liposome-mediated gene transfer may introduce plasmids into host cells, the majority of the transferred DNA is lost, most likely due to lysosomal degradation (French, *Herz*, 18, 222–229 (1993)). As sufficient expression of therapeutic genes to treat disease is a major obstacle in gene therapy, other means of gene transfer are needed in order to ensure the success of gene therapy protocols.

In addition to the identification and development of ideal vectors, another tool needed for the success of gene therapy in the clinic is therapeutic factors and the nucleic acids that encode them. Ideally, a therapeutic factor for use in gene therapy has utility in treating a number of afflictions, and can be delivered and expressed in vivo. One such factor, pigment epithelium-derived factor (PEDF), has recently been identified and realized to have both neurotrophic and anti-angiogenic properties. Regrettably, PEDF is almost solely generated in human fetus retinal cells. The poor production of PEDF from retinal pigment epithelial (RPE) cells and the scarcity of the source tissue of PEDF complicates the use of this potentially valuable therapeutic factor in the clinic.

Given the hurdles associated with gene therapy, in particular the difficulties associated with efficient expression of appropriate therapeutic factors, there remains a need in the art for an expression vector comprising a coding sequence for a therapeutic factor that potentially can aid in the treatment of a number of afflictions. The present invention provides such an expression vector. This and other advantages of the present invention will become apparent from the detailed description provided herein.

BRIEF SUMMARY OF THE INVENTION

The present invention provides a viral vector comprising a nucleic acid sequence encoding pigment epithelium-derived factor (PEDF) or a therapeutic fragment thereof. The nucleic acid sequence is operably linked to regulatory sequences necessary for expression of PEDF or a therapeutic fragment thereof. Preferably, the viral vector is an adenoviral vector or an adeno-associated viral vector. Also preferably, the viral vector further comprises one or more additional nucleic acid sequences encoding therapeutic substances other than PEDF or a therapeutic fragment thereof.

DESCRIPTION OF THE PREFERRED EMBODIMENTS

The present invention is directed to a viral vector comprising a nucleic acid sequence encoding pigment epithelium-derived factor (PEDF) or a therapeutic fragment thereof. The nucleic acid sequence is operably linked to regulatory sequences necessary for expression of PEDF or a therapeutic fragment thereof. The combined efficiency of viral vectors to deliver nucleic acids to host cells and the therapeutic potential of PEDF had not been realized prior to the present invention. As such, the present invention provides a powerful tool for the prophylactic and therapeutic treatment of disease, as well as gene therapy and disease research.

Viral vectors for use in the present invention include, for example, retroviral vectors, herpes simplex virus (HSV)-based vectors, parvovirus-based vectors, e.g., adeno-associated virus (AAV)-based vectors, AAV-adenoviral chimeric vectors, and adenovirus-based vectors. Any of these viral vectors can be prepared using standard recombinant DNA techniques described in, e.g., Sambrook et al., *Molecular Cloning, a Laboratory Manual*, 2d edition, Cold Spring Harbor Press, Cold Spring Harbor, N.Y. (1989), and Ausubel et al., *Current Protocols in Molecular Biology*, Greene Publishing Associates and John Wiley & Sons, New York, N.Y. (1994).

Retrovirus is an RNA virus capable of infecting a wide variety of host cells. Upon infection, the retroviral genome integrates into the genome of its host cell and is replicated along with host cell DNA, thereby constantly producing viral RNA and any nucleic acid sequence incorporated into the retroviral genome. As such, long-term expression of a therapeutic factor(s) is achievable when using retrovirus. Retroviruses contemplated for use in gene therapy are relatively non-pathogenic, although pathogenic retroviruses exist. When employing pathogenic retroviruses, e.g., human immunodeficiency virus (HIV) or human T-cell lymphotrophic viruses (HTLV), care must be taken in altering the viral genome to eliminate toxicity to the host. A retroviral vector additionally can be manipulated to render the virus replication-deficient. As such, retroviral vectors are thought to be particularly useful for stable gene transfer in vivo. Lentiviral vectors, such as HIV-based vectors, are exemplary of retroviral vectors used for gene delivery. Unlike other retroviruses, HIV-based vectors are known to incorporate their passenger genes into non-dividing cells and, therefore, can be of use in treating persistent forms of disease.

HSV-based viral vectors are suitable for use as an expression vector to introduce nucleic acids into numerous cell types. The mature HSV virion consists of an enveloped icosahedral capsid with a viral genome consisting of a linear double-stranded DNA molecule that is 152 kb. Most replication-deficient HSV vectors contain a deletion to remove one or more intermediate-early genes to prevent replication. Advantages of the herpes vector are its ability to enter a latent stage that can result in long-term DNA expression, and its large viral DNA genome that can accommodate exogenous DNA inserts of up to 25 kb. Of course, this ability is also a disadvantage in terms of short-term treatment regimens. However, one of ordinary skill in the art has the ability to determine the appropriate vector for a particular situation. For a description of HSV based vectors appropriate for use in the present inventive methods, see, for example, U.S. Pat. Nos. 5,837,532; 5,846,782; 5,849,572; and 5,804,413 and International Patent Applications WO 91/02788, WO 96/04394, WO 98/15637, and WO 99/06583.

The viral vector of the present invention can be an AAV vector. AAV vectors are viral vectors of particular interest for use in gene therapy protocols. AAV is a DNA virus, which is not known to cause human disease. The AAV genome is comprised of two genes, rep and cap, flanked by inverted terminal repeats (ITRs), which contain recognition signals for DNA replication and packaging for the virus. AAV requires co-infection with a helper virus (i.e., an adenovirus or a herpes virus), or expression of helper genes, for efficient replication. AAV can be propagated in a wide array of host cells including human, simian, and rodent cells, depending on the helper virus employed. AAV vectors used for administration of a therapeutic nucleic acid typically have approximately 96% of the parental genome deleted, such that only the ITRs remain. This eliminates immunologic or toxic side effects due to expression of viral genes. In addition, delivering the AAV rep protein enables integration of the AAV vector comprising AAV ITRs into a specific region of genome, if desired. Host cells comprising an intergrated AAV genome show no change in cell growth or morphology (see, for example, U.S. Pat. No. 4,797,368). As such, prolonged expression of therapeutic factors from AAV vectors can be useful in treating persistent and chronic diseases.

Adenovirus (Ad) is a 36 kb double-stranded DNA virus that efficiently transfers DNA in vivo to a variety of different target cell types. Adenovirus used in vivo is preferably made replication-deficient by deleting one or more select genes required for viral replication. The expendable E3 region is also frequently deleted to allow additional room for a larger DNA insert. The vector can be produced in high titers and can efficiently transfer DNA to replicating and non-replicating cells. The newly transferred genetic information remains epi-chromosomal, thus eliminating the risks of random insertional mutagenesis and permanent alteration of the genotype of the target cell. However, if desired, the integrative properties of AAV can be conferred to adenovirus by constructing an AAV-Ad chimeric vector. For example, the AAV ITRs and nucleic acid encoding the Rep protein incorporated into an adenoviral vector enables the adenoviral vector to integrate into a mammalian cell genome. Therefore, AAV-Ad chimeric vectors are an interesting option for use in the present invention.

Preferably, the viral vector of the present inventive method is an adenoviral vector. In the context of the present invention, the adenoviral vector can be derived from any serotype of adenovirus. Adenoviral stocks that can be employed as a source of adenovirus can be amplified from the adenoviral serotypes 1 through 51, which are currently available from the American Type Culture Collection (ATCC, Rockville, Md.), or from any other serotype of adenovirus available from any other source. For instance, an adenovirus can be of subgroup A (e.g., serotypes 12, 18, and 31), subgroup B (e.g., serotypes 3, 7, 11, 14, 16, 21, 34, and 35), subgroup C (e.g., serotypes 1, 2, 5, and 6), subgroup D (e.g., serotypes 8, 9, 10, 13, 15, 17, 19, 20; 22–30, 32, 33, 36–39, and 42–47), subgroup E (serotype 4), subgroup F (serotypes 40 and 41), or any other adenoviral serotype. Preferably, the adenovirus is a subgroup C adenovirus, e.g., serotype 2 or 5. However, non-group C adenoviruses also can be used to prepare replication-deficient adenoviral gene transfer vectors comprising a nucleic acid sequence encoding PEDF or a therapeutic fragment thereof. Preferred adenoviruses used in the construction of non-group C adenoviral gene transfer vectors include Ad12 (group A), Ad7 (group B), Ad9 and Ad36 (group D), Ad4 (group E), and Ad41 (group F). Non-group C adenoviral vectors, methods of producing non-group C adenoviral vectors, and methods of using non-group C adenoviral vectors are disclosed in, for example, U.S. Pat. Nos. 5,801,030; 5,837,511; and 5,849,561 and International Patent Applications WO 97/12986 and WO 98/53087. Adenoviral vectors, methods of producing adenoviral vectors, and methods of using adenoviral vectors are disclosed in, for example, U.S. Pat. Nos. 5,851,806 and 5,994,106 and International Patent Applications WO 95/34671 and WO 97/27826.

The adenoviral vector is preferably deficient in at least one gene function required for viral replication, thereby resulting in a "replication-deficient" adenoviral vector. Preferably, the adenoviral vector is deficient in at least one essential gene function of the E1 region of the adenoviral genome. In addition to a deficiency in the E1 region, the recombinant adenovirus also can have a mutation in the major late promoter (MLP). The mutation in the MLP can be in any of the MLP control elements such that it alters the responsiveness of the promoter, as discussed in International Patent Application WO 00/00628. More preferably, the vector is deficient in at least one essential gene function of the E1 region and at least part of the E3 region (e.g., an Xba I deletion of the E3 region). With respect to the E1 region, the adenoviral vector can be deficient in at least part of the E1a region and at least part of the E1b region. Preferably, the adenoviral vector is "multiply deficient," meaning that the adenoviral vector is deficient in one or more essential gene functions required for viral replication in each of two or more regions. For example, the aforementioned E1-deficient or E1-, E3-deficient adenoviral vectors can be further deficient in at least one essential gene of the E4 region. Adenoviral vectors deleted of the entire E4 region can elicit lower host immune responses.

Alternatively, the adenoviral vector lacks all or part of the E1 region and all or part of the E2 region. However, adenoviral vectors lacking all or part of the E1 region, all or part of the E2 region and all or part of the E3 region also are contemplated herein and are well-known in the art. In one embodiment, the adenoviral vector lacks all or part of the E1 region, all or part of the E2 region, all or part of the E3 region, and all or part of the E4 region. Suitable replication-deficient adenoviral vectors are disclosed in U.S. Pat. No. 5,851,806 and 5,994,106 and International Patent Applications WO 95/34671 and WO 97/21826. For example, suitable replication-deficient adenoviral vectors include those with at least a partial deletion of the E1a region, at least a partial deletion of the E1b region, at least a partial deletion of the E2a region, and at least a partial deletion of the E3 region. Alternatively, the replication-deficient adenoviral vector can have at least a partial deletion of the E1 region, at least a partial deletion of the E3 region, and at least a partial deletion of the E4 region. One of ordinary skill in the art will appreciate that other regions of the adenoviral genome can be deleted in order to modulate the properties of the adenoviral vector or create additional room for nucleic acid inserts. For example, the adenoviral DNA polymerase gene can be deleted in an E1/E3 deficient vector to produce a viable vector for gene transfer.

Therefore, in a preferred embodiment, the viral vector of the present invention is a multiply-deficient adenoviral vector lacking all or part of the E1 region, all or part of the E3 region, all or part of the E4 region, and, optionally, all or part of the E2 region. In this regard, it has been observed that an at least E4-deficient adenoviral vector expresses a transgene at high levels for a limited amount of time in vivo and that persistence of expression of a transgene in an at least E4-deficient adenoviral vector can be modulated through the action of a trans-acting factor, such as HSV ICP0, Ad pTP, CMV-IE2, CMV-IE86, HIV-tat, HTLV-tax, HBV-X, AAV-Rep78, the cellular factor from the U20S osteosarcoma cell line that functions like HSV ICP0, or the cellular factor in PC12 cells that is induced by nerve growth factor, among others. In view of the above, the at least E4 deficient adenoviral vector preferably further comprises a nucleic acid sequence encoding a trans-acting factor that modulates the persistence of expression of the nucleic acid sequence encoding PEDF or a therapeutic fragment thereof. Alternatively, the viral vector of the present invention can be co-introduced into a host cell with a second expression vector comprising a nucleic acid sequence encoding a trans-acting factor that modulates the expression of the nucleic acid sequence encoding PEDF or a therapeutic fragment thereof. Preferably, the nucleic acid sequence encoding the trans-acting factor does not encode an adenoviral E4 region gene product. Whether expressed from the adenoviral vector or supplied by a second expression vector, preferably, the transacting factor is the *Herpes simplex* infected cell polypeptide 0 (HSV ICP0).

The present inventive adenoviral vector includes a spacer to provide viral growth in a complementing cell line similar to that achieved by singly replication deficient adenoviral vectors, particularly a singly replication deficient E1 deficient adenoviral vector. In the preferred E4$^-$ adenoviral vector of the present invention wherein the L5 fiber region is retained, the spacer is desirably located between the L5 fiber region and the right-side ITR. More preferably in such an adenoviral vector, the E4 polyadenylation sequence alone or, most preferably, in combination with another sequence exists between the L5 fiber region and the right-side ITR, so as to sufficiently separate the retained L5 fiber region from the right-side ITR, such that viral production of such a vector approaches that of a singly replication deficient adenoviral vector, particularly a singly replication deficient E1 deficient adenoviral vector.

In the absence of a spacer, production of fiber protein and/or viral growth of the multiply replication deficient adenoviral vector is reduced by comparison to that of a singly replication deficient adenoviral vector. However, inclusion of the spacer in at least one of the deficient adenoviral regions, preferably the E4 region, counteracts this defect in growth and fiber expression.

The function of the replication deficient region is provided by a complementing cell line. As a result, the spacer does not need to provide the deficient function and can be any sequence, limited only by the size of the insert that the vector will accommodate. The spacer alone can function to repair the growth defect and decreased fiber expression found in multiply replication deficient adenoviral vectors. The spacer can be of any suitable size, desirably at least about 15 base pairs (e.g., between about 15 base pairs and about 12,000 base pairs), preferably about 100 base pairs to about 10,000 base pairs, more preferably about 500 base pairs to about 8,000 base pairs, even more preferably about 1,500 base pairs to about 6,000 base pairs, and most preferably about 2,000 to about 3,000 base pairs.

The spacer can contain any sequence or sequences which are of the desired length. The spacer sequence can be coding or non-coding and native or non-native with respect to the adenoviral genome, but does not restore the replication function to the deficient region. The spacer can also contain a promoter-variable expression cassette. More preferably, the spacer comprises an additional polyadenylation sequence and/or a passenger gene. Preferably, in the case of a spacer inserted into a region deficient for E4, both the E4 polyadenylation sequence and the E4 promoter of the adenoviral genome or any other (cellular or viral) promoter remain in the vector. The spacer is located between the E4 polyadenylation site and the E4 promoter, or, if the E4 promotor is not present in the vector, the spacer is proximal to the right-side ITP.

The spacer can comprise any suitable polyadenylation sequence. Examples of suitable polyadenylation sequences include synthetic optimized sequences. BGH (Bovine Growth Hormone), polyoma virus, TK (Thymidine Kinase), EBV (Epstein Barr Virus) and the papillomaviruses, including human papillomaviruses and BPV (Bovine Papilloma Virus). Preferably, particularly in the E4 deficient region, the spacer includes an SV40 polyadenylation sequence. The SV40 polyadenylation sequence allows for higher virus production levels of multiply replication deficient adenoviral vectors.

Although a passenger gene is typically inserted into the E1 deficient region of an adenoviral genome, a passenger gene can also function as the spacer in the E4 deficient region of the adenoviral genome. The passenger gene is limited only by the size of the fragment the vector can accommodate and can be any suitable gene. Examples of suitable passenger genes include marker gene sequences such as pGUS, secretory alkaline phosphatase, luciferase, B-galactosidase, and human anti-trypsin; therapeutic genes of interest such as the cystic fibrosis transmembrane regulator gene (CFTR); and potential immune modifiers such as B3-19K, E3-14.7, ICP47, fas lipand gene, and CTLA4 gene.

It should be appreciated that the deletion of different regions of the viral vector, e.g., the adenoviral vector, once administered to an animal, can alter the immune response of the animal to the vector. In particular, deletion of different regions can reduce the inflammatory response generated by the adenoviral vector. Furthermore, the adenoviral vector's coat protein can be modified so as to decrease the adenoviral vector's ability or inability to be recognized by a neutralizing antibody directed against the wild-type coat protein, as described in International Patent Application WO 98/46509. Such modifications are useful for long-term treatment of persistent or chronic disease.

Similarly, the coat protein of a viral vector, preferably an adenoviral vector, can be manipulated to alter the binding specificity or recognition of a virus for a viral receptor on a potential host cell. For adenovirus, such manipulations can include deletion of regions of the fiber, penton, or hexon, insertions of various native or non-native ligands into portions of the coat protein, and the like. Manipulation of the coat protein can broaden the range of cells infected by a viral vector or enable targeting of a viral vector to a specific cell type. For example, in one embodiment, the viral vector comprises a chimeric coat protein (e.g., a fiber, hexon, pIX, pIIIa, or penton protein), which differs from the wild-type (i.e., native) coat protein by the introduction of a nonnative amino acid sequence, preferably at or near the carboxyl terminus. Preferably, the nonnative amino acid sequence is inserted into or in place of an internal coat protein sequence. One of ordinary skill in the art will understand that the nonnative amino acid sequence can be inserted within the internal coat protein sequence or at the end of the internal coat protein sequence. The resultant chimeric viral coat protein is able to direct entry into cells of the viral, i.e., adenoviral, vector comprising the coat protein that is more efficient than entry into cells of a vector that is identical except for comprising a wild-type viral coat protein rather than the chimeric viral coat protein. Preferably, the chimeric virus coat protein binds a endogenous binding site present on the cell surface that is not recognized, or is poorly recognized by a vector comprising a wild-type viral coat protein. One direct result of this increased efficiency of entry is that the virus, preferably, the adenovirus, can bind to and enter numerous cell types which a virus comprising wild-type coat protein typically cannot enter or can enter with only a low efficiency.

In another embodiment of the present invention, the viral vector comprises a chimeric virus coat protein not selective for a specific type of eukaryotic cell. The chimeric coat protein differs from the wild-type coat protein by an insertion of a nonnative amino acid sequence into or in place of an internal coat protein sequence. In this embodiment, the chimeric virus coat protein efficiently binds to a broader range of eukaryotic cells than a wild-type virus coat, such as described in International Patent Application WO 97/20051.

With respect to adenovirus, specificity of binding to a given cell can also be adjusted by use of an adenovirus comprising a short-shafted adenoviral fiber gene, as discussed in U.S. Pat. No. 5,962,311. Use of an adenovirus comprising a short-shafted adenoviral fiber gene reduces the level or efficiency of adenoviral fiber binding to its cell-surface receptor and increases adenoviral penton base binding to its cell-surface receptor, thereby increasing the specificity of binding of the adenovirus to a given cell. Alternatively, use of an adenovirus comprising a short-shafted fiber facilitates targeting of the adenovirus to a desired cell-surface receptor by the introduction of a nonnative amino acid sequence either into the penton base or the fiber knob.

The ability of a viral vector to recognize a potential host cell can be modulated without genetic manipulation of the coat protein. For instance, complexing an adenovirus with a bispecific molecule comprising a penton base-binding domain and a domain that selectively binds a particular cell surface binding site enables one of ordinary skill in the art to target the vector to a particular cell type.

Suitable modifications to a viral vector, specifically an adenoviral vector, are described in U.S. Pat. Nos. 5,559,099; 5,731,190; 5,712,136; 5,770,442; 5,846,782; 5,926,311; 5,965,541; and 6,057,155 and International Patent Applications WO 96/07734, WO 96/26281, WO 97/20051, WO 98/07865, WO 98/07877, WO 98/40509, WO 98/54346, and WO 00/15823. Similarly, the construction of viral vectors is well understood in the art. Adenoviral vectors can be constructed and/or purified using the methods set forth, for example, in U.S. Pat. No. 5,965,358 and International Patent Applications WO 98/56937, WO 99/15686, and WO 99/54441. Adeno-associated viral vectors can be constructed and/or purified using the methods set forth, for example, in U.S. Pat. No. 4,797,368 and Laughlin et al., *Gene*, 23, 65–73 (1983).

According to the invention, the nucleic acid sequence encoding PEDF or a therapeutic fragment thereof is operably linked to regulatory sequences necessary for expression, i.e., a promoter. A "promoter" is a DNA sequence that directs the binding of RNA polymerase and thereby promotes RNA synthesis. A nucleic acid sequence is "operably linked" to a promoter when the promoter is capable of directing transcription of that nucleic acid sequence. A promoter can be native or non-native to the nucleic acid sequence to which it is operably linked.

Any promoter (i.e., whether isolated from nature or produced by recombinant DNA or synthetic techniques) can be used in connection with the present invention to provide for transcription of the nucleic acid sequence. The promoter preferably is capable of directing transcription in a eukaryotic (desirably mammalian) cell. The functioning of the promoter can be altered by the presence of one or more enhancers and/or silencers present on the vector. "Enhancers" are cis-acting elements of DNA that stimulate or inhibit transcription of adjacent genes. An enhancer that inhibits transcription also is termed a "silencer." Enhancers differ from DNA-binding sites for sequence-specific DNA binding proteins found only in the promoter (which also are termed "promoter elements") in that enhancers can function in either orientation, and over distances of up to several kilobase pairs (kb), even from a position downstream of a transcribed region. Therefore, promoter regions can vary in length and sequence and can further encompass one or more DNA binding sites for sequence-specific DNA binding proteins and/or an enhancer or silencer. Enhancers and/or silencers can similarly be present on a nucleic acid sequence outside of the promoter per se.

Transcription of PEDF or a therapeutic fragment thereof can be directed by a viral promoter. Suitable viral promoters are known in the art and include, for instance, cytomegalovirus (CMV) promoters, such as the CMV immediate-early promoter, promoters derived from human immunodeficiency virus (HIV), such as the HIV long terminal repeat promoter, Rous sarcoma virus (RSV) promoters, such as the RSV long terminal repeat, mouse mammary tumor virus (MMTV) promoters, HSV promoters, such as the herpes thymidine kinase promoter (Wagner et al., *Proc. Natl. Acad. Sci.*, 78, 144–145 (1981)) or the Lap 2 promoter, promoters derived from SV40 or Epstein Barr virus, an adeno-associated viral promoter, such as the p5 promoter, an adenoviral promoter, such as the Ad2 or Ad5 major late promoter and tripartite leader, and the like.

Many of the above-identified viral promoters are constitutive promoters. Such promoters, as well as mutations thereof, are known and have been described in the art (see, e.g., Boshart et al., *Cell*, 41, 521–530 (1985)). Others suitable promoters for use in the methods of the present invention include the regulatory sequences of the metallothionine gene (Brinster et al., *Nature*, 296, 39–42 (1982)), promoter elements from yeast or other fungi such as the Gal 4 promoter, the alcohol dehydrogenase promoter, the phosphoglycerol kinase promoter, and the alkaline phosphatase promoter. Similarly, promoters isolated from the genome of mammalian cells, such as the β-actin promoter, the muscle-creatine promoter, or the elongation factor 1α (EF1α) promoter, can be employed.

Instead of being a constitutive promoter, the promoter can be an inducible promoter, i.e., a promoter that is up- and/or down-regulated in response to appropriate signals. For instance, the regulatory sequences can comprise a hypoxia driven promoter. Other examples of suitable inducible promoter systems include, but are not limited to, the IL-8 promoter, the metallothionine inducible promoter system, the bacterial lacZYA expression system, the tetracycline expression system, and the T7 polymerase system. Further, promoters that are selectively activated at different developmental stages (e.g., globin genes are differentially transcribed from globin-associated promoters in embryos and adults) can be employed.

For example, the promoter sequence that regulates expression of PEDF or a therapeutic fragment thereof can contain at least one heterologous regulatory sequence responsive to regulation by an exogenous agent. The regulatory sequences are preferably responsive to exogenous agents such as, but not limited to, drugs, hormones, or other gene products. For example, the regulatory sequences, e.g., promoter, preferably are responsive to glucocorticoid receptor-hormone complexes, which, in turn, enhance the level of transcription of PEDF or a therapeutic fragment thereof.

The regulatory sequences also can comprise a tissue-specific promoter, i.e., a promoter that is preferentially activated in a given tissue and results in expression of a gene product in the tissue where activated. A typically used tissue-specific promoter is a myocyte-specific promoter. A promoter exemplary of a myocyte-specific promoter is the myosin light-chain 1A promoter. A tissue-specific promoter for use in the present inventive vector can be chosen by the ordinarily skilled artisan based upon the target tissue or cell-type. For example, if the present inventive vector is to be administered to the eye, a promoter specific to ocular tissue, such as a rhodopsin promoter, can be employed. Examples of rhodopsin promoters include, but are not limited to, a GNAT cone-transducing alpha-subunit gene promoter and an interphotoreceptor retinoid binding protein promoter.

One of ordinary skill in the art will appreciate that each promoter drives transcription, and, therefore, protein expression, differently with respect to time and amount of protein produced. For example, the CMV promoter is characterized as having peak activity shortly after transduction, i.e., about 24 hours after transduction, then quickly tapering off. On the other hand, the RSV promoter's activity increases gradually, reaching peak activity several days after transduction, and maintains a high level of activity for several weeks. Indeed, sustained protein expression driven by an RSV promoter in an adenoviral vector is observed in all cell types studied, including, for instance, liver cells, lung cells, spleen cells, diaphragm cells, skeletal muscle cells, and cardiac muscle cells. Thus, a promoter can be selected for use in the methods of the present invention by matching its particular pattern of activity with the desired pattern and level of expression of PEDF or a therapeutic fragment thereof. Alternatively, a hybrid promoter can be constructed which combines the desirable aspects of multiple promoters. For example, a CMV-RSV hybrid promoter combining the CMV promoter's initial rush of activity with the RSV promoter's high maintenance level of activity would be especially preferred for use in many embodiments of the present inventive method. It is also possible to select a promoter with an expression profile that can be manipulated by the investigator.

Also preferably, the adenoviral vector comprises a nucleic acid sequence encoding a cis-acting factor, wherein the cis-acting factor modulates the expression of the nucleic acid sequence encoding PEDF or a therapeutic fragment thereof. In this regard, it has been observed that the persistence of a transgene in an at least E4-deficient adenoviral vector can be modulated through the action of a cis-acting factor, such as matrix attachment region (MAR) sequences (e.g., immunoglobulin heavy chain µ (murine; Jenuwein et al., *Nature*, 385(16), 269 (1997)), locus control region (LCR) sequences, or apolipoprotein B (human; Kalos et al., *Molec. Cell. Biol.*, 15(1): 198–207 (1995)), among others. MAR sequences have been characterized as DNA sequences that associate with the nuclear matrix after a combination of nuclease digestion and extraction (Bode et al., *Science*, 255 (5041), 195–197 (1992)). MAR sequences are often associated with enhancer-type regulatory regions and, when integrated into genomic DNA, MAR sequences augment transcriptional activity of adjacent nucleotide sequences. It has been postulated that MAR sequences play a role in controlling the topological state of chromatin structures, thereby facilitating the formation of transcriptionally-active complexes. Similarly, it is believed LCR sequences function to establish and/or maintain domains permissive for transcription. Many LCR sequences give tissue specific expression of associated nucleic acid sequences. Addition of MAR or LCR sequences to the expression vector can further enhance expression of PEDF or a therapeutic fragment thereof.

The construction of an exogenous nucleic acid operably linked to regulatory sequences necessary for expression is well within the skill of the art (see, for example, Sambrook et al., *Molecular Cloning: A Laboratory Manual*, 2d ed.

(1989)). With respect to promoters, nucleic acid sequences, and the like, located on a viral vector according to the present invention, such elements can be constructed as part of a cassette, either independently or coupled. In the context of the present invention, a "cassette" is a particular base sequence that possesses functions which facilitate subcloning and recovery of nucleic acid sequences (e.g., one or more restriction sites) or expression (e.g., polyadenylation or splice sites) of particular nucleic acid sequences. With respect to the expression of nucleic acid sequences according to the present invention, the ordinary skilled artisan is aware that different genetic signals and processing events control levels of nucleic acids and proteins/peptides in a cell, such as, for instance, transcription, mRNA translation, and post-transcriptional processing. Transcription of DNA into RNA requires a functional promoter, as described herein.

Protein expression is dependent on the level of RNA transcription that is regulated by DNA signals, and the levels of DNA template. Similarly, translation of mRNA requires, at the very least, an AUG initiation codon, which is usually located within 10 to 100 nucleotides of the 5' end of the message. Sequences flanking the AUG initiator codon have been shown to influence its recognition by eukaryotic ribosomes, with conformity to a perfect Kozak consensus sequence resulting in optimal translation (see, e.g., Kozak, *J. Molec. Biol.*, 196, 947–950 (1987)). Also, successful expression of an exogenous nucleic acid in a cell can require post-translational modification of a resultant protein. Thus, production of a protein can be affected by the efficiency with which DNA (or RNA) is transcribed into mRNA, the efficiency with which mRNA is translated into protein, and the ability of the cell to carry out post-translational modification. These are all factors of which the ordinary skilled artisan is aware and is capable of manipulating using standard means to achieve the desired end result.

Along these lines, to optimize protein production, preferably the nucleic acid sequence is operatively linked to a polyadenylation site. Also, preferably all the proper transcription signals (and translation signals, where appropriate) are correctly arranged such that the nucleic acid sequence are properly expressed in the cells into which it is introduced. If desired, the viral vector also can comprise splice sites (i.e., splice acceptor and splice donor sites) to facilitate mRNA production. Moreover, if the viral vector comprises a nucleic acid sequence encoding a protein or peptide other than PEDF or a therapeutic fragment thereof, which is a processed or secreted protein or acts intracellularly, preferably the nucleic acid sequence further comprises the appropriate sequences for processing, secretion, intracellular localization, and the like.

In certain embodiments, it may be advantageous to modulate expression of PEDF or a therapeutic fragment thereof. An especially preferred method of modulating expression of a nucleic acid sequence comprises addition of site-specific recombination sites on the expression vector. Contacting an expression vector comprising site-specific recombination sites with a recombinase will either up- or down-regulate transcription of a coding sequence, or simultaneously up-regulate transcription one coding sequence and down-regulate transcription of another, through the recombination event. Use of site-specific recombination to modulate transcription of a nucleic acid sequence is described, for example, U.S. Pat. Nos. 5,801,030 and 6,063,627 and International Patent Application WO 97/09439.

The viral vector of the present invention comprises a nucleic acid sequence encoding PEDF or a therapeutic fragment thereof. The nucleic acid sequence encoding PEDF can be obtained from any source, e.g., isolated from nature, synthetically generated, isolated from a genetically engineered organism, and the like. PEDF, also named early population doubling factor-1 (EPC-1), is a secreted protein having homology to a family of serine protease inhibitors named serpins. PEDF is made predominantly by retinal pigment epithelial cells and is detectable in most tissues and cell types of the body. PEDF has both neurotrophic and anti-angiogenic properties and, therefore, is useful in the treatment and study of a broad array of diseases. Neurotrophic factors are thought to be responsible for the maturation of developing neurons and for maintaining adult neurons. It has been postulated that neurotrophic factors can actually reverse degradation of neurons associated with, for example, vision loss. Neurotrophic factors function in both paracrine and autocrine fashions, making them ideal therapeutic agents. In this regard, PEDF has been observed to induce differentiation in retinoblastoma cells and enhance survival of neuronal populations (Chader, *Cell Different.*, 20, 209–216 (1987)). PEDF further has gliastatic activity or has the ability to inhibit glial cell growth. As discussed above, PEDF also has anti-angiogenic activity. Anti-angiogenic derivatives of PEDF include SLED proteins, discussed in WO 99/04806. It also has been postulated that PEDF is involved with cell senescence (Pignolo et al., *J. Biol. Chem.*, 268 (12), 8949–8957 (1998)). PEDF is further characterized in U.S. Pat. No. 5,840,686 and International Patent Applications WO 93/24529 and WO 99/04806.

The viral vector, e.g. the adenoviral or the adeno-associated viral vector, also can comprise a nucleic acid sequence encoding a therapeutic fragment of PEDF. One of ordinary skill in the art will appreciate that any anti-angiogenic factor or neurotrophic factor, e.g., PEDF, can be modified or truncated and retain anti-angiogenic or neurotrophic activity. As such, therapeutic fragments of PEDF (i.e., those fragments having biological activity sufficient to, for example, inhibit angiogenesis or promote neuron survival) also are suitable for incorporation into the present inventive viral vector. Also suitable for incorporation into the viral vector are nucleic acid sequences comprising substitutions, deletions, or additions, but which encode a functioning PEDF peptide or a therapeutic fragment thereof. Likewise, fusion protein comprising PEDF or a therapeutic fragment thereof and for example, a moiety that stabilizes peptide conformation, also can be present into the present inventive viral vector. A functioning PEDF peptide or a therapeutic fragment thereof prevents or ameliorates neovascularization. In that PEDF also has neurotrophic activity, a functioning PEDF peptide or a therapeutic fragment thereof desirably promotes neuronal cell differentiation, inhibits glial cell proliferation, and/or promotes neuronal cell survival. One of ordinary skill in the art will understand that complete prevention or amelioration of neovascularization is not required in order to realize a therapeutic effect. Likewise, complete induction of neuron survival or differentiation is not required in order to realize a benefit. Therefore, both partial and complete prevention and amelioration of angiogenesis or promotion of neuron survival is appropriate. The ordinarily skilled artisan has the ability to determine whether a modified PEDF or a fragment of PEDF has neurotrophic and anti-angiogenic therapeutic activity using, for example, neuronal cell differentiation and survival assays (see, for example, U.S. Pat. No. 5,840,686), the mouse ear model of neovascularization, the rat hindlimb ischemia model, or the methods of Examples 1 and 2.

In addition to the above, the viral vector comprising a nucleic acid sequence encoding PEDF or a therapeutic fragment thereof can further comprise one or more additional nucleic acid sequences encoding a therapeutic substance(s) other than PEDF or a therapeutic fragment thereof. Desirably, the expression of the therapeuatic substance is beneficial; e.g., prophylactically or therapeutically beneficial, to the host cell. If the therapeutic substance confers a prophylactic or therapeutic benefit to the cell, the therapeutic substance can exert its effect at the level of RNA or protein. For example, the therapeutic substance can be an additional anti-angiogenic factor or neurotrophic factor other than PEDF or a therapeutic fragment thereof, or can be a peptide other than an anti-angiogenic factor or neurotrophic factor that can be employed in the treatment of a disorder. Alternatively, the therapeutic substance can be an antisense molecule, a ribozyme, a protein that affects splicing or 3' processing (e.g., polyadenylation), or a protein that affects the level of expression of another gene within the cell (i.e., where gene expression is broadly considered to include all steps from initiation of transcription through production of a process protein), such as by mediating an altered rate of mRNA accumulation or transport or an alteration in post-transcriptional regulation. Preferably, the therapeutic substance is a neurotrophic factor, such as ciliary neurotrophic factor (CNTF). CNTF belongs to the neuropoietic cytokines subclass of neurotrophic factors. CNTF promotes the survival of ciliary ganglionic neurons and supports certain neurons that are nerve growth factor (NGF)-responsive.

Alternatively, one or more additional nucleic acid sequences encoding a therapeutic substance(s) can encode a factor associated with cell differentiation. Preferably, the therapeutic substance is an atonal-associated peptide such as Math1 or Hath1 or a biologically active fragment of either of the foregoing. Math1 is a member of the mouse basic helix-loop-helix family of transcription factors and is homologous to the *Drosophila* gene *atonal*. Hath1 is the human counterpart of Math1. Math1 has been shown to be essential for hair development and can stimulate hair regeneration in the ear. Combining the neurotrophic properties of PEDF and the hair cell differentiation properties of an atonal-associated peptide provides a powerful tool for the treatment and research of, for example, sensory disorders. Math1 is further characterized in, for example, Bermingham et al., *Science*, 284, 1837–1841 (1999) and Zheng and Gao, *Nature Neuroscience*, 3(2), 580–586 (2000).

One or more additional nucleic acid sequences encoding therapeutic substances can encode an anti-angiogenic substance other than PEDF or a therapeutic fragment thereof. An anti-angiogenic substance is any biological factor that prevents or ameliorates neovascularization. One of ordinary skill in the art will understand that the anti-angiogenic substance can effect partial or complete prevention and amelioration of angiogenesis to achieve a therapeutic effect. An anti-angiogenic substance includes, for instance, an anti-angiogenic factor, an anti-sense molecule specific for an angiogenic factor, a ribozyme, a receptor for an angiogenic factor, and an antibody that binds a receptor for an angiogenic factor.

Anti-angiogenic factors include, for example, angiostatin, vasculostatin, endostatin, platelet factor 4, heparinase, interferons (e.g., INFα), and the like. One of ordinary skill in the art will appreciate that any anti-angiogenic factor can be modified or truncated and retain anti-angiogenic activity. As such, active fragments of anti-angiogenic factors (i.e., those fragments having biological activity sufficient to inhibit angiogenesis) are also useful for incorporation into the present inventive viral vector.

An anti-sense molecule specific for an angiogenic factor should generally be substantially identical to at least a portion, preferably at least about 20 continuous nucleotides, of the nucleic acid encoding the angiogenic factor to be inhibited, but need not be identical. The anti-sense nucleic acid molecule can be designed such that the inhibitory effect applies to other proteins within a family of genes exhibiting homology or substantial homology to the nucleic acid. The introduced anti-sense nucleic acid molecule also need not be full-length relative to either the primary transcription product or fully processed mRNA. Generally, higher homology can be used to compensate for the use of a shorter sequence. Furthermore, the anti-sense molecule need not have the same intron or exon pattern, and homology of non-coding segments will be equally effective. Antisense phosphorothiotac oligodeoxynucleotides (PS-ODNs) is exemplary of an anti-sense molecule specific for an angiogenic factor.

Ribozymes can be designed that specifically pair with virtually any target RNA and cleave the phosphodiester backbone at a specific location, thereby functionally inactivating the target RNA. In carrying out this cleavage, the ribozyme is not itself altered and is, thus, capable of recycling and cleaving other molecules, making it a true enzyme. The inclusion of ribozyme sequences within anti-sense RNAs confers RNA-cleaving activity upon them, thereby increasing the activity of the constructs. The design and use of target RNA-specific ribozymes is described in Haseloffet al., *Nature*, 334, 585–591 (1988). Preferably, the ribozyme comprises at least about 20 continuous nucleotides complementary to the target sequence on each side of the active site of the ribozyme.

Receptors specific for angiogenic factors inhibit neovascularization by sequestering growth factors away from functional receptors capable of promoting a cellular response. For example, soluble VEGF-R1 (flt-1), VEGF-R2 (flk/kdr), and VEGF-R3 (flt-4)receptors, as well as VEGF-receptor chimeric proteins, compete with VEGF receptors on vascular endothelial cells to inhibit endothelial cell growth (Aiello, *PNAS*, 92, 10457 (1995)). Preferably, the viral vector of the present invention comprises at least one nucleic acid sequence encoding soluble flt receptor in addition to the nucleic acid sequence encoding PEDF or a therapeutic fragment thereof. Receptors specific for angiogenic factors, in particular the soluble flt receptor, and use thereof to inhibit angiogenesis is further described in Kendall et al., *PNAS*, 90(22), 10705–10709 (1993), Kong et al., *Human Gene Therapy*, 9, 823–833 (1988), and International Patent Application WO 94/21679. Also contemplated are growth factor-specific antibodies and fragments thereof (e.g., Fab, F(ab')$_2$, and Fv) that neutralize angiogenic factors (e.g., VEGF) or bind receptors for angiogenic factors.

The nucleic acid sequence encoding PEDF or a therapeutic fragment thereof and any nucleic acid sequence encoding a therapeutic substance other than PEDF or a therapeutic fragment thereof can be operably linked to different promoters. As discussed herein, different promoters have dissimilar levels and patterns of activity. One of ordinary skill in the art will appreciate the freedom to dictate the expression of different coding sequences through the use of multiple promoters. Preferably, the nucleic acid sequence encoding PEDF or a therapeutic fragment thereof is operably linked to a RSV promoter and one or more additional nucleic acids sequences is operably linked to a CMV promoter, or vice versa. Alternatively, the multiple coding sequences can be operably linked to the same promoter to form a polycistronic element. The polycistronic element is transcribed into a single mRNA molecule when transduced into the ocular cell. Translation of the mRNA molecule is initiated at each coding sequence, thereby producing the multiple, separate peptides simultaneously. On the other hand, the nucleic acid sequence encoding PEDF or a therapeutic fragment thereof and at least one additional nucleic acid sequence encoding a different therapeutic substance can be linked to a bi-directional promoter.

In addition to a nucleic acid sequence encoding PEDF or a therapeutic fragment thereof and optionally a nucleic acid encoding a different therapeutic substance, the viral vector also can comprise a selection gene or a nucleic acid sequence encoding marker protein, such as green fluorescent protein or luciferase. Selection genes are useful in vector construction protocols. Marker proteins also are useful in vector construction and in determining vector migration. Marker proteins can further be used to determine points of injection or treated tissues in order to efficiently space injections of the expression vector to provide a widespread area of gene transfer, if desired. The additional nucleic acid sequence(s) encoding the therapeutic substance or marker protein can be part of an expression cassette.

It should be appreciated that any of the nucleic acid sequences described herein can be altered from their native form to increase their therapeutic effect. For example, a cytoplasmic form of a therapeutic nucleic acid can be converted to a secreted form by incorporating an endoplasmic reticular localization signal peptide into the encoded gene product. The therapeutic substance and/or PEDF or a therapeutic fragment thereof can be designed to be taken up by neighboring cells by fusion of the peptide with VP22, HIV tat, and the like. This allows a cell comprising the nucleic acid sequence to have a therapeutic effect on a number of surrounding cells.

To facilitate storage and, optionally, administration, the viral vector desirably is part of a pharmaceutical composition, which comprises a pharmaceutically acceptable carrier and the viral vector. Any suitable pharmaceutically acceptable carrier can be used within the context of the present invention, and such carriers are well known in the art. The choice of carrier will be determined, in part, by the particular site to which the composition is to be administered and the particular method used to administer the composition. The composition also can comprise agents which facilitate uptake of the viral vector into host cells. Suitable composition formulations include aqueous and non-aqueous solutions, isotonic sterile solutions, which can contain antioxidants, buffers, bacteriostats, and solutes that render the formulation isotonic with the blood or intraocular fluid of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets of the kind previously described. Preferably, the pharmaceutically acceptable carrier is a buffered saline solution. More preferably, the viral vector is present in a pharmaceutical composition formulated to protect the expression vector from damage prior to administration. For example, the pharmaceutical composition can be formulated to reduce loss of the viral vector on devices used to prepare, store, or administer the viral vector, such as glassware, syringes, or needles. The pharmaceutical composition can be formulated to decrease the light sensitivity and/or temperature sensitivity of the expression vector. To this end, the pharmaceutical composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a pharmaceutical composition will extend the shelf life of the vector and facilitate administration of the viral vector.

In addition, one of ordinary skill in the art will appreciate that the viral vector of the present invention can be present in a composition with other therapeutic or biologically-active agents. For example, therapeutic factors useful in the treatment of a particular indication can be present. For instance, if treating vision loss, hyaluronidase can be added to a composition to effect the break down of blood and blood proteins in the vitreous of the eye. Factors that control inflammation, such as ibruprofen, can be part of the composition to reduce swelling and inflammation associated with in vivo administration of the viral vector. Antiangiogenic factors, such as soluble growth factor receptors, growth factor antagonists, i.e., angiotensin, and the like can also be part of the composition, as well as additional neurotrophic factors. Similarly, vitamins and minerals, antioxidants, and micronutrients can be co-administered. Antibiotics, i.e., microbicides and fungicides, can be present to reduce the risk of infection associated with gene transfer procedures and other disorders.

EXAMPLES

The following examples further illustrate the present invention but, of course, should not be construed as in any way limiting its scope.

Example 1

This example demonstrates a method of determining whether a PEDF protein or fragment thereof has therapeutic activity.

An adenoviral vector deficient in one or more essential gene functions of the E1, E3, and E4 regions of the adenoviral genome and comprising a PEDF gene or fragment thereof (Ad.PEDF) is preferably constructed as set forth in WO 99/15686 (McVey et al.).

Several in vivo models of ocular neovascularization are available. Neovascularization of the retina is obtained in, for example, neonatal animals, i.e., neonatal mice, by exposing the mice to hypoxic conditions shortly after birth. Several days later, the neonatal mice are exposed to standard atmospheric conditions, resulting in ischemia-induced neovascularization of the retina.

Ad.PEDF is administered to the right eye of at least 12 day old mice anesthetized with, for example, ketamine or a combination of ketamine and xylazine via intravitreal injection. Injections are performed by forming an entrance site in the posterior portion of the eye and administering approximately 0.1–5.0 µl of composition comprising Ad.PEDF. In most instances, an injection of the expression vector will be administered to only one eye, while the remaining eye serves as a control. The mice are sacrificed at various time points after administration to determine the extent and duration of PEDF expression in the retina. The right and left eyes of each animal are enucleated and either fixed for histological analysis or prepared for PEDF expression analysis. If desired, detection of PEDF DNA, PEDF RNA, or PEDF protein can be accomplished using methods well known in the art, such as PCR and blotting techniques (see, for example, Sambrook et al., supra).

To determine the effect of PEDF on neovascularization in vivo in, for example, a human, indirect ophthalmoscopy of the retina is ideal. Stereophotographs are useful in detecting extensive neovascularization, but not appropriate for detecting subtle lesions. Other methods of monitoring neovascularization include fluorescein angiography, which is useful in determining vascular leakage, color fundus photography, scanning electron microscopy of the retinal layer, and vascular casts. Any of the above techniques is appropriate for determining whether a PEDF peptide or fragment thereof has therapeutic activity. For example, a PEDF peptide or therapeutic fragment thereof desirably inhibits or ameliorates neovascularization of the retina compared to animals treated with null-vectors or other negative controls.

Example 2

The following example demonstrates a method of determining the effect of PEDF or a therapeutic fragment thereof on neovascularization.

An adenoviral vector deficient in one or more essential gene functions of the E1, E3, and E4 regions of the adenoviral genome and comprising a PEDF gene (Ad.PEDF) is constructed as set forth in WO 99/15686 (McVey et al.).

An in vivo model of choroidal neovascularization can be obtained by detaching the retina of an eye of, for example, a mouse or rabbit, and debriding the pigmented epithelia. Choriocapillary regeneration is monitored in both treated and untreated eyes. Ad.PEDF is administered prior to perturbing the retinal pigment epithelial (RPE) to determine the effect of the present inventive method in preventing choroidal neovascularization. Of course, Ad.PEDF is administered after perturbing the retina and RPE for determining the therapeutic effect of the procedure on neovascularization.

Choroidal neovascularization can be monitored in vivo using fundus photography, fluorescein angiography, and/or indocyanine-green angiography, as commonly used in the art. Using these methods, one of ordinary skill in the art is able to detect growth of new blood vessels and vascular leakage associated with neovascularization. For research purposes, neovascularization also can be determined by enucleating the eyes and preparing vascular casts or examining. ocular tissue via scanning electron microscopy.

All references cited herein are hereby incorporated by reference to the same extent as if each reference was individually and specifically indicated to be incorporated by reference and was set forth in its entirety herein.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A replication deficient adenoviral vector comprising an adenovirus serotype 5 genome and comprising a nucleic acid sequence encoding pigment epithelium-derived factor (PEDF) or a therapeutic fragment thereof, wherein (a) the nucleic acid sequence is operably linked to a CMV promoter, (b) the adenoviral vector is rendered replication deficient by deletion of all of the E1 region and by deletion of a portion of the E4 region, and (c) the adenoviral vector comprises a pGUS spacer sequence in place of the deleted portion of the E4 region, wherein the pGUS spacer sequence comprises an SV40 polyadenylation sequence.

2. The adenoviral vector of claim 1, wherein the adenoviral vector is lacking all or part of the E3 region.

3. The adenoviral vector of claim 2, wherein the adenoviral vector comprises a nucleic acid sequence encoding a cis-acting factor, wherein the cis-acting factor modulates the expression of the nucleic acid sequence encoding PEDF or a therapeutic fragment thereof.

4. The adenoviral vector of claim 3, wherein the cis-acting factor is a MAR sequence or a LCR sequence.

5. The adenoviral vector of claim 2, wherein the adenoviral vector further comprises a nucleic acid sequence encoding a trans-acting factor, wherein the trans-acting factor modulates the expression of the nucleic acid sequence encoding PEDF or a therapeutic fragment thereof, and wherein the nucleic acid sequence encoding a trans-acting factor does not encode an adenoviral E4 region gene product.

6. The adenoviral vector of claim 5, wherein the trans-acting factor is selected from the group consisting of HSV ICP0, Ad pTP, CMV UL84, VZV-ORF61, PRV-EP0, CMV-E1, CMV-IE2, CMV-IE86, HIV-tat, HTLV-tax, HBV-X, and AAV-Rep 78.

7. The adenoviral vector of claim 1, wherein the adenoviral vector comprises a chimeric coat protein comprising a nonnative amino acid sequence, wherein the chimeric virus coat protein directs entry into cells of a vector comprising the chimeric virus coat protein that is more efficient than entry into cells of a vector that is identical except for comprising a wild-type virus coat protein rather than the chimeric virus protein, and wherein the chimeric virus coat protein binds an endogenous binding site present on the cell surface not recognized by a vector comprising a wild-type virus coat protein.

8. The adenoviral vector of claim 7, wherein the nonnative amino acid sequence is inserted into or in place of an internal coat protein sequence.

9. The adenoviral vector of claim 1, wherein the adenoviral vector comprises a chimeric virus coat protein comprising a nonnative amino acid sequence inserted into or in place of an internal coat protein sequence, wherein the chimeric virus coat protein efficiently binds to a broader range of eukaryotic cells than a wild-type virus coat protein and wherein the chimeric virus coat protein is not selective for a specific type of eukaryotic cell.

10. The adenoviral vector of claim 1 further comprising one or more additional nucleic acid sequences encoding therapeutic substances other than PEDF or a therapeutic fragment thereof.

11. The adenoviral vector of claim 10, wherein one or more additional nucleic acid sequences encodes an anti-angiogenic substance.

12. The adenoviral vector of claim 11, wherein the anti-angiogenic substance is a soluble receptor specific for an angiogenic factor.

13. The adenoviral vector of claim 12, wherein the soluble receptor specific for an angiogenic factor is a soluble VEGF-R1 receptor.

14. The adenoviral vector of claim 10, wherein the therapeutic substances other than PEDF or a therapeutic fragment thereof are linked to an endoplasmic reticulum localization signal peptide.

15. The adenoviral vector of claim 1, wherein the adenoviral vector comprises a nucleic acid sequence encoding PEDF.

* * * * *